United States Patent
Janssens et al.

(10) Patent No.: US 8,379,964 B2
(45) Date of Patent: Feb. 19, 2013

(54) DETECTING SEMICONDUCTOR SUBSTRATE ANOMALIES

(75) Inventors: Dominque Janssens, Antwerp (BE); Luc Vanderheydt, Wilsele (BE); Johan DeGreeve, Leuven (BE); Lieve Govaerts, Heverlee (BE)

(73) Assignee: KLA-Tencor Corporation, Milpitas, CA (US)

( * ) Notice: Subject to any disclaimer, the term of this patent is extended or adjusted under 35 U.S.C. 154(b) by 273 days.

(21) Appl. No.: 12/674,232

(22) PCT Filed: Aug. 29, 2008

(86) PCT No.: PCT/EP2008/061414
§ 371 (c)(1),
(2), (4) Date: Feb. 19, 2010

(87) PCT Pub. No.: WO2009/027517
PCT Pub. Date: Mar. 5, 2009

(65) Prior Publication Data
US 2011/0123091 A1    May 26, 2011

(30) Foreign Application Priority Data
Aug. 31, 2007  (EP) .................. 07115449

(51) Int. Cl.
  *G06K 9/00*    (2006.01)
(52) U.S. Cl. .................. 382/145; 356/237.1; 356/237.6
(58) Field of Classification Search .................. 382/145, 382/141; 356/237.2–237.6
See application file for complete search history.

(56) References Cited

U.S. PATENT DOCUMENTS

| | | | | |
|---|---|---|---|---|
| 5,098,191 A * | 3/1992 | Noguchi et al. | ............... | 356/394 |
| 5,638,465 A * | 6/1997 | Sano et al. | .................... | 382/281 |
| 6,256,091 B1 | 7/2001 | Kobayashi | | |
| 6,630,996 B2 * | 10/2003 | Rao et al. | .................... | 356/237.5 |
| 7,601,555 B2 | 10/2009 | Kim et al. | | |
| 8,077,305 B2 * | 12/2011 | Owen et al. | ................ | 356/237.1 |
| 2002/0089664 A1 | 7/2002 | Shibata et al. | | |
| 2002/0154810 A1 | 10/2002 | Hakim | | |
| 2004/0012775 A1 | 1/2004 | Kinney | | |

FOREIGN PATENT DOCUMENTS

| | | |
|---|---|---|
| EP | 1801569 | 6/2007 |
| JP | 04-216904 | 8/1992 |
| JP | 05-119468 | 5/1993 |
| JP | 07-301609 | 11/1995 |
| JP | 08-220008 | 8/1996 |
| JP | 2007-218638 | 8/2007 |
| WO | 2005100961 | 10/2005 |

* cited by examiner

*Primary Examiner* — Tarifur Chowdhury
*Assistant Examiner* — Isiaka Akanbi
(74) *Attorney, Agent, or Firm* — Luedeka Neely Group, P.C.

(57) ABSTRACT

The present invention is directed to a method for detecting anomalies in a semiconductor substrate comprising the steps of providing a semiconductor substrate, making an inspection image I of the substrate, generating an image K from image I by image processing, generating image B by binarizing image K, and examining image I using image B, characterized in that generating image K comprises multiplying a high-pass convolution filtered image G(I) from image I and a first weight image W1. The present invention is also directed to an apparatus suitable for applying the method.

7 Claims, 5 Drawing Sheets

DETECTING SEMICONDUCTOR SUBSTRATE ANOMALIES

This application claims all rights and priority on prior pending PCT application serial number PCT/EP2008/061414 filed Aug. 29, 2008 and EP application serial number 07115449.6 filed Aug. 31, 2007. The present invention relates to an apparatus and method for detecting anomalies in semiconductor substrates.

FIELD OF THE INVENTION

Background of the Invention

In semiconductor processing and manufacturing of semiconductor components and integrated circuits, quality control is very important at every stage of the manufacturing process. This quality control is to a high extend directed to detection of defects, in particular semiconductor substrate anomalies, such as cracks and micro-cracks, scratches, dirt, voids, etc. Since even micro-cracks, penetrating or non-penetrating in the substrate, can cause breaking of the substrate during further processing, it is very important to be able to detect these cracks in an early stage of processing. For example for solar cell production, polycrystalline silicon substrates are used which are very brittle. If micro-cracks are present, likely the substrate will break during further processing.

Quality control of a semiconductor substrate relies heavily on optical inspection, because for detecting anomalies optical inspection methods are beneficial in terms of throughput compared to other inspection methods.

A common method to optically detect anomalies on semiconductor substrates compares an image of the substrate part to be inspected with an image of such substrate part containing substantially no anomalies of at least any anomalies of the kind to be detected. The first is usually called the inspection image, while the latter is usually called the reference image. To compare both images, the reference image is then subtracted from the inspection image. The pixel values which after subtraction are higher than a fixed threshold value are labeled as surface anomaly.

However, this method can only be applied if the reference image has substantially the same gray values, i.e. the same background image, as the inspection image. Further, it can only be applied if there is no geometrical variation, e.g. scaling or distortion, between the inspection and reference image, and if both images can be well aligned in order to subtract images from exactly corresponding substrate parts from each other and in order to not cause false positives by misalignment.

In some cases a reference image having substantially the same gray values as the inspection image is unavailable simply because the semiconductor substrate to be inspected is never identical to a corresponding substrate which could be used as reference surface.

An example demonstrating the shortcomings of a referential inspection method is the inspection of polycrystalline silicon substrates used in solar cell production. The pattern of crystal boundaries at their surface is never identical. Consequently, a reference image having the same gray values as the inspection image can never be captured.

Methods and apparatuses have been proposed to potentially alleviate the above problem. For example in "Solar Cell Crack Inspection by Image Processing", Fu Zhuang, et al. propose a so-called non-referential method, i.e. an inspection method wherein no reference image is used. Gauss-Laplacian 5×5 filtering is used to sharpen the image, which is computationally quite expensive. Furthermore, only test results on solar cells with rather homogeneous pattern are presented.

Another method and also an apparatus for detecting micro-cracks are described in DE-A1-10 2005 061 785, wherein the substrate is illuminated with infrared backlight and visible diffuse front light and wherein two substrate images are captured and image processed. To capture both images at different wavelengths, two cameras with different focal planes are needed, which is expensive and which requires a very accurate calibration of both cameras.

A second example of a method and apparatus for detecting micro-cracks is described in EP-A1-0 985 924, wherein front infrared illumination above 2 microns in a certain angle is applied. To that extend, an expensive low resolution camera is used.

Given the above drawbacks of prior art methods and apparatuses, it is an objective of the present invention to provide a method and apparatus for detecting semiconductor substrate anomalies, such as cracks, scratches, voids, pits, or foreign material included in the substrate, in a non-referential way in order to be able to select defective semiconductor substrates.

In particular, it is an object of the present invention to provide a method and apparatus for detecting micro-cracks, penetrating and non-penetrating, in poly-silicon substrates.

It is further an objective of the present invention to provide a method and apparatus for detecting semiconductor substrate anomalies including micro-cracks in a less expensive way compared to known prior art methods and apparatuses.

The present invention meets the above objectives by providing a method which comprises image processing using multiplication of a high-pass convolution filtered image and a weight image and by providing an apparatus for performing such method, preferably using a single camera.

SUMMARY OF THE INVENTION

The present invention is directed to a method for detecting anomalies in a semiconductor substrate comprising the steps of:
  a. providing a semiconductor substrate
  b. making an inspection image I of the substrate
  c. generating an image K from image I by image processing
  d. generating image B by binarizing image K
  e. examining image I using image B characterized in that step c comprises multiplying a high-pass convolution filtered image G(I) from image I and a first weight image W1.

Further, the invention is directed to an apparatus for detecting anomalies in a semiconductor substrate comprising:
  a. means for holding a semiconductor substrate
  b. a backlight for illuminating the substrate's backside
  c. a diffuse front light for illuminating the substrate's front side
  d. an image processing unit
  e. a camera characterized in that the wavelengths of the backlight and diffuse front light are within identical ranges.

DETAILED DESCRIPTION OF THE INVENTION

A person skilled in the art will understand that the embodiments described below are merely illustrative in accordance with the present invention and not limiting the intended scope of the invention. Other embodiments may also be considered.

Figure 1:
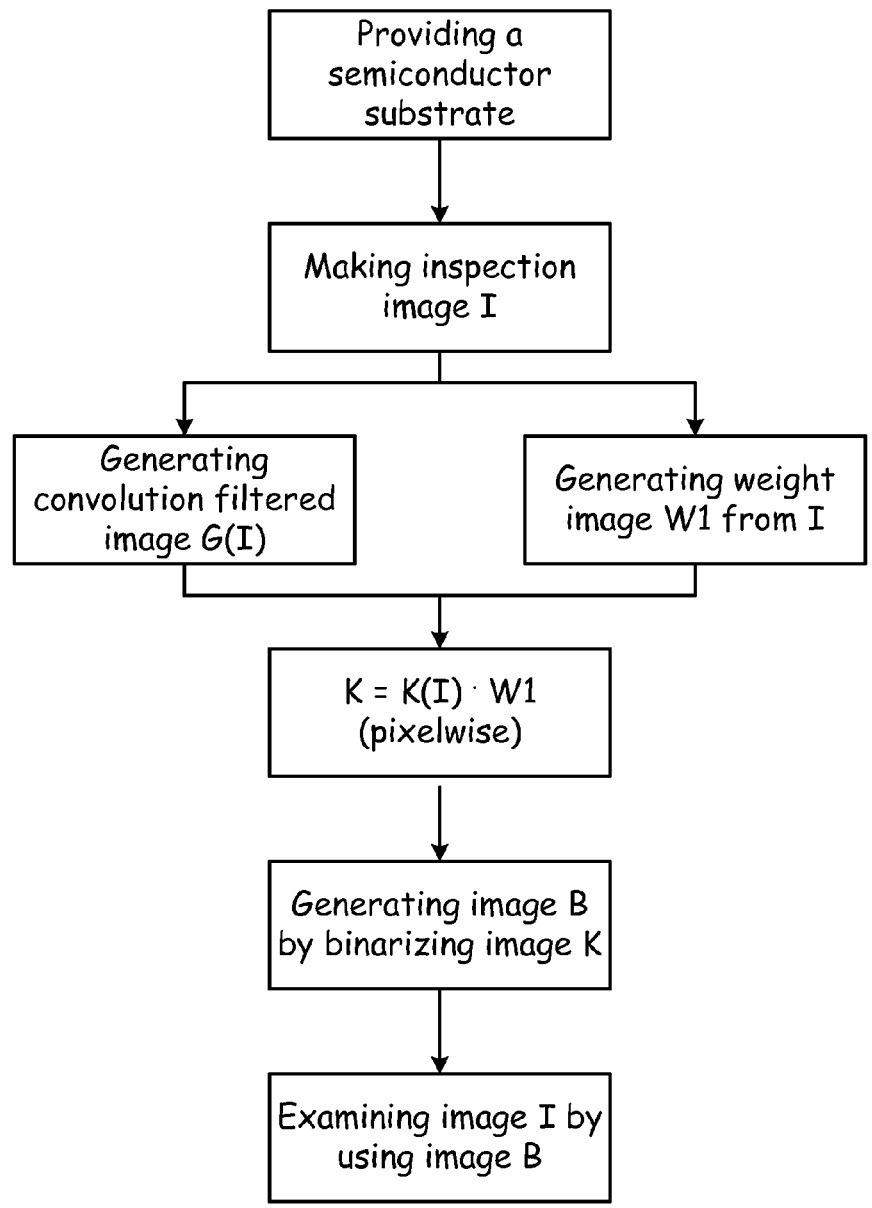
FIG. 1 illustrates an embodiment of a method according to the present invention.

As a first embodiment and as illustrated in FIG. 1, the present invention provides a method for detecting anomalies in a semiconductor substrate comprising the steps of
 a. providing a semiconductor substrate
 b. making an inspection image I of the substrate
 c. generating an image K from image I by image processing
 d. generating image B by binarizing image K
 e. examining image I using image B
 characterized in that generating image K comprises multiplying a high-pass convolution filtered image G(I) from image I and a first weight image W1.

Depending on the filter kernel, convolution filtering may attenuate low-frequency image content, whilst passing or even accentuating the high frequencies. In the context of the present invention, high-pass convolution filtering is used in order to accentuate in G(I) anomalies like micro-cracks and voids, but also crystal boundaries. These convolution filters are characterized by the large, weight at the centre of the pixel neighborhood, surrounded by smaller, mostly opposite signed weights. The value of the centre pixel dominates the calculation of the new pixel value, whilst the surrounding values help to reduce the effect of the large weight. This gives the effect of accentuating regions of large, rapid change in pixel value, and making areas of constant pixel value almost unaffected.

By multiplying a high-pass convolution filtered image G(I) from image I and a first weight image W1, surface anomalies and in particular micro-cracks may be distinguished from crystal boundaries, thereby enabling to detect these anomalies even in case of semiconductor substrates with non-repetitive pattern such as poly-silicon and to select defective substrates.

Generating high-pass convolution filtered image G(I) may be realized by a Laplacian filter. As an alternative to high-pass convolution filtering, also multi-directional convolution filtering such as a Gabor filter may be used.

In one embodiment of the method in accordance with the present invention, the first weight image W1 may be generated by fuzzy weighting of image I. A fuzzy weighting function gives for example pixels with a grey value within a certain range a weight value between 0 and 1. Pixels with grey values below the range may get weight value 0 and pixels with grey values above the range may get weight value 1, or any other function depending on the kind of substrate anomaly to be detected. The fuzzy weighting function may be implemented as a lookup table.

In another embodiment of the method in accordance with the present invention, the first weight image W1 may be generated by threshold filtering, meaning binarizing image I.

In a preferred embodiment of the present invention, G(I) may be generated by a 3×3 Laplace convolution filter and the first weight image W1 may be generated by threshold filtering image I.

The step of making an inspection image I may comprise illuminating the substrate with a backlight having wavelengths where the substrate is transparent or semitransparent. Anomalies should be less transparent than the substrate or not transparent within the same wavelength range. In case of silicon substrates, the wavelength range should be in the near infrared band (NIR), and preferably between about 950 nanometer and about 1 micrometer, because silicon is transparent above 1 micrometer, semitransparent about 950 nanometer and opaque for shorter wavelengths. At these wavelengths a camera with a standard silicon based sensor may be used.

Figure 2:
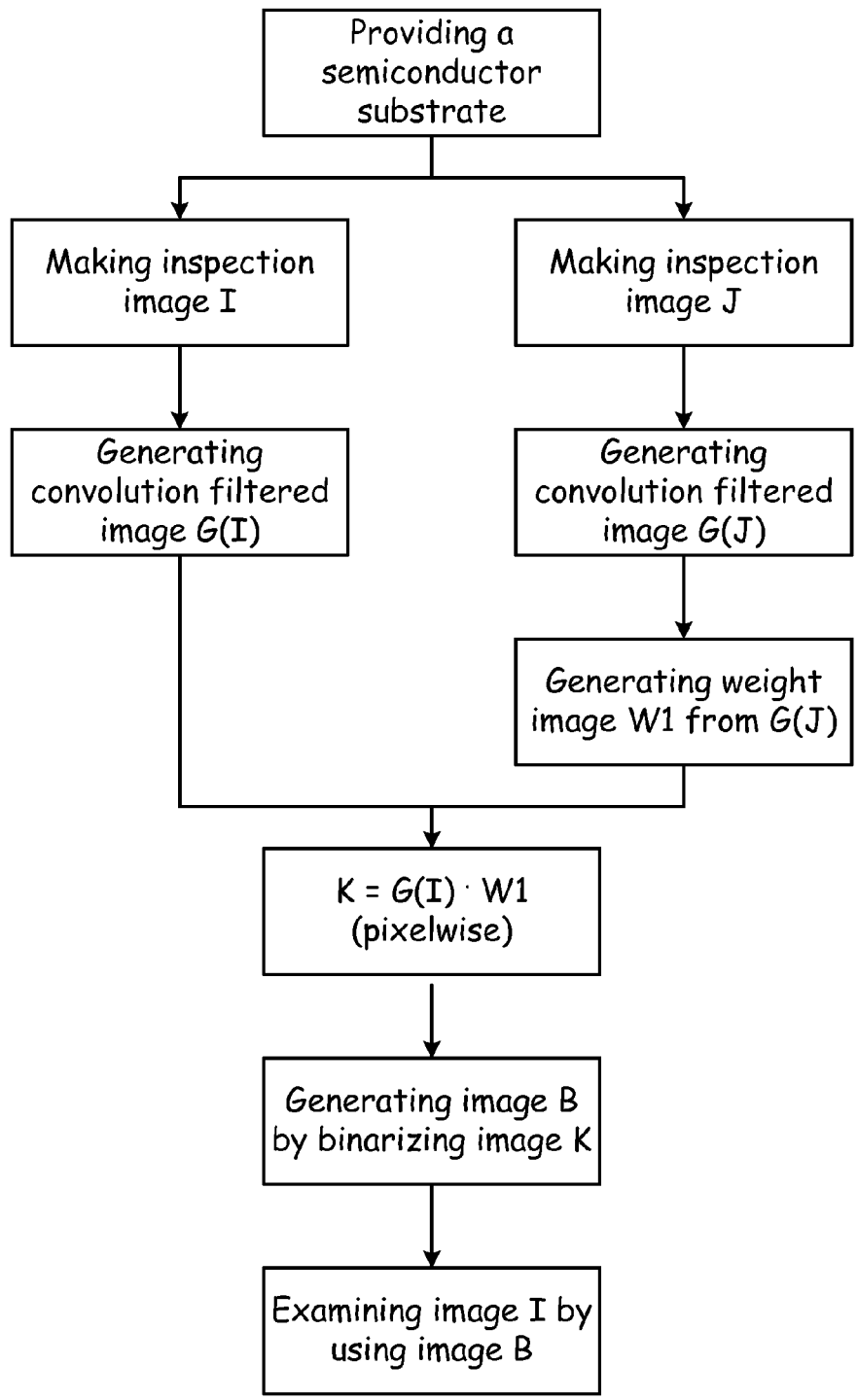
FIG. 2 illustrates another embodiment of a method according to the present invention.

In a further embodiment in accordance with the present invention and as illustrated in FIG. 2, the method may further comprise a step b' of making an image J of the substrate, and wherein first weight image W1 is generated by fuzzy weighting or threshold filtering of a high-pass convolution filtered image G(J) from image J.

Image J may be captured while illuminating the substrate with diffuse front light wherein the substrate is semitransparent. Anomalies should be less transparent than the substrate or not transparent within the same wavelength range. In case of silicon substrates, the wavelength range should be within the near infrared band (NIR), and preferably around about 950 nanometer. In a more preferred embodiment, the backlight for capturing image I and the diffuse front light for capturing image J may have an identical wavelength range, because then a single camera keeping the same focus can be used to capture both pictures.

In a preferred embodiment, G(I) may be generated by a 3×3 Laplace convolution filter and the first weight image W1 may be generated by threshold filtering of G(J) which may be generated by a 3×3 Laplace convolution filter.

In a further embodiment, the method may further comprise the step multiplying convolution filtered image G(I) with a second weight image W2 from image I. Second weight image W2 may be generated by fuzzy weighting or threshold filtering of image I.

In an embodiment in accordance with the present invention, the method may be used for detecting penetrating and/or non-penetrating micro-cracks in semiconductor substrates. In particular, penetrating and/or non-penetrating micro-cracks may be detected in non-repetitive patterned substrates such as polycrystalline silicon.

All methods in accordance with the present invention may be extended by a step of region growing, wherein, after the easiest detectable cracks are found, a starting pixel in these cracks (i.e. a seed point) is chosen to start the region growing (i.e. clustering).

The methods in accordance with the present invention only using backlight may be extended with repeating the method by searching the area around found cracks, therefore generating an additional weight image with a broader threshold range. By using this extension, also the ends of a crack, which are usually thinner and less penetrating than the center of the crack, may be detected.

Figure 3:
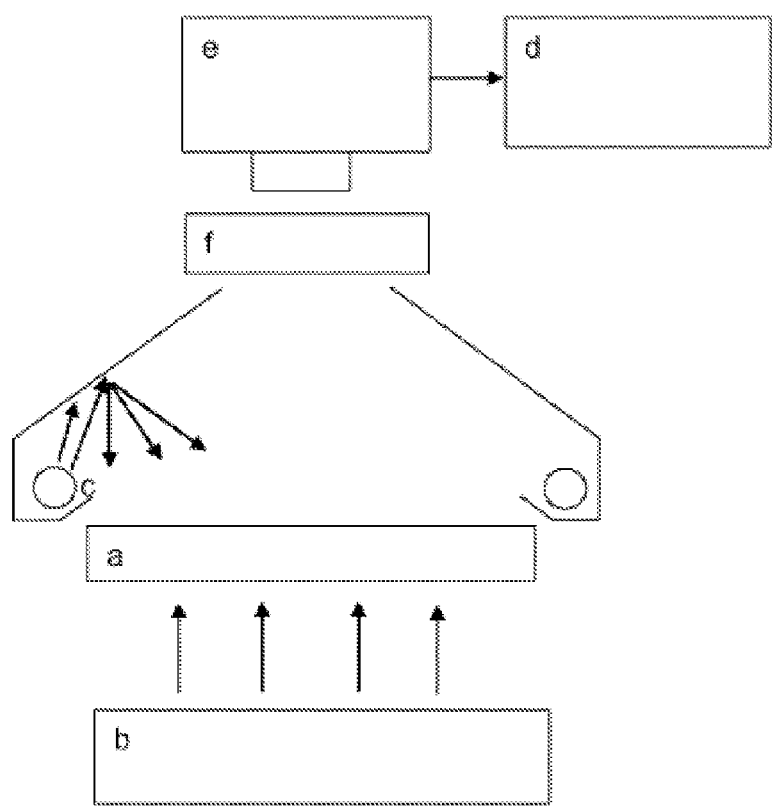
FIG. 3 illustrates an embodiment of an apparatus according to the present invention.

In another embodiment and as illustrated in FIG. 3, the present invention provides an apparatus for detecting anomalies in a semiconductor substrate comprising
 a. means for holding a semiconductor substrate (a)
 b. a backlight for illuminating the substrate's backside (b)
 c. a diffuse front light for illuminating the substrate's front side (c)
 d. an image processing unit (d)
 e. a camera (e)
 characterized in that the wavelengths of the backlight and diffuse front light are within identical ranges.

By using substantially the same wavelength range for backlight and diffuse front light illumination, preferably a single camera keeping the same focus can be used to capture images when illuminating them with backlight or illuminating them with diffuse front light. Both images may be image processed by the image processing unit to detect substrate anomalies, in particular both penetrating and non-penetrating micro-cracks.

The apparatus may also further comprise an optical filter (f) blocking visible light.

In an embodiment in accordance with the present invention, the apparatus may use wavelengths where the substrate is semitransparent. Anomalies should be less transparent than the substrate or not transparent within the same wavelength range. In case of silicon substrates, the wavelength range should be within the NIR range, preferably between about 935 nanometer and about 965 nanometer, and more preferably around about 950 nanometer, because silicon is semitransparent at about 950 nanometer and opaque for shorter wavelengths. At these wavelengths a camera with a standard silicon based sensor may be used.

In a preferred embodiment, the backlight and/or the diffuse front light comprises LEDs which are mounted with a distance between two LEDs and at a distance from the semiconductor substrate such that the light of each LED overlaps light of at least on other LED. By overlapping the light beams, the light is diffused and is more robust against non-homogeneity of the LEDs without additional use of diffuser.

EXAMPLE 1

Figure 4:
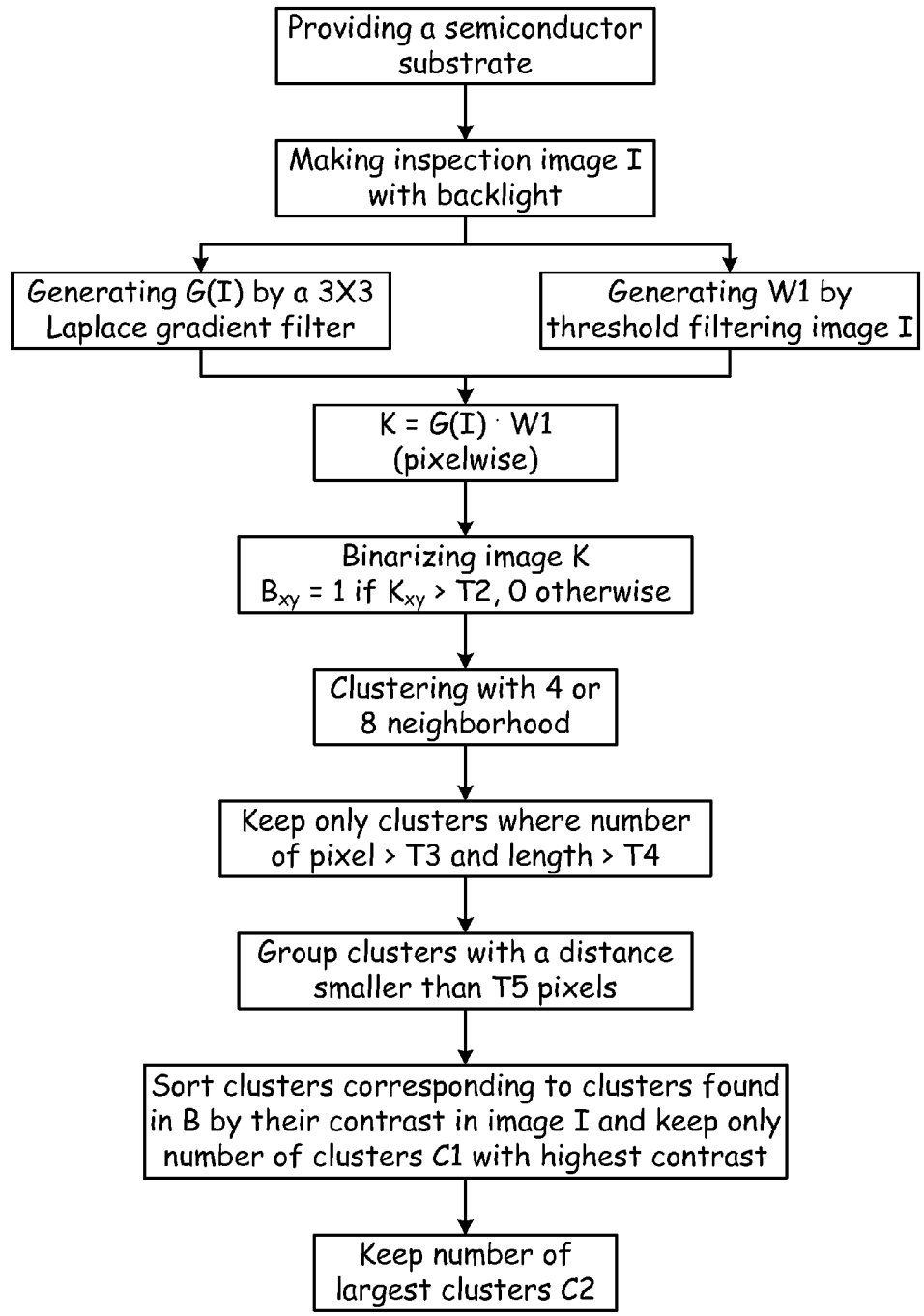
FIG. 4 illustrates a first example in accordance with the present invention.

As illustrated in FIG. 4, a first example in accordance with the present invention is described below.

A semiconductor substrate is provided on a means for holding a semiconductor substrate. The substrate is illuminated with a 950 nanometer backlight and an inspection image I is captured by a camera with a resolution between about 50 and about 100 micrometer/pixel. Inspection image I and all derived images have 8 bit grey values, i.e. from 0 to 255.

An image G(I) is generated by a 3×3 Laplace convolution filter, for example $$\begin{array}{ccc} 1 & 1 & 1 \\ 1 & -8 & 1 \\ 1 & 1 & 1 \end{array}$$

which accentuates anomalies, such as cracks, voids, foreign material included in the substrate, and crystal boundaries from image I.

Further, an weight image W1 is generated by binarizing (threshold filtering) image I, wherein $$W1_{xy} = \begin{cases} 1 & \text{if } T0 \le I_{xy} \le T1 \\ 0 & \text{otherwise} \end{cases}$$

(x and y are pixel coordinates)

where preferably
for non-penetrating cracks, voids, foreign material $T0=0$; $T1=150$
for penetrating cracks $T0=205$; $T1=255$ Hence G(I) and W1 are pixelwise multiplied in order to distinguish between crystal boundaries and other anomalies and the resulting image K is binarized wherein $$B_{xy} = \begin{cases} 1 & \text{if } K_{xy} > T2 \\ 0 & \text{otherwise} \end{cases}$$

where T2 is preferably 85.

The image I is examined using image B. Therefore, in image B clustering is done with 4 neighborhood (taking only 2 vertical and 2 horizontal neighborhood pixels in account) or 8 neighborhood (taking also diagonal neighborhood pixels in account). Of these clusters, only clusters where Number of pixels>T3 AND length>T4 are kept, with T3 is preferably 10 and T4 is preferably 20. Then, clusters with a distance smaller than T5 pixels are grouped, where T5 is preferably 3. Based on this group of clusters in image B, the corresponding clusters of pixels in image I are sorted by their contrast and only a number of clusters C1 (preferably 100) with the highest contrast are kept. Thereof, a number C2 (preferably 10) of the largest clusters are kept.

The method as illustrated in example 1 may be extended by repeating the method by searching the area around found cracks, therefore generating an image W1 wherein $$W1_{xy} = \begin{cases} 1 & \text{if } T0 \le I_{xy} \le T1 \\ 0 & \text{otherwise} \end{cases}$$

where preferably $T0=0$; $T1=230$.

By using this extension also the ends of a crack, which are usually thinner and less penetrating than the center of the crack, may be detected.

EXAMPLE 2

Figure 5:
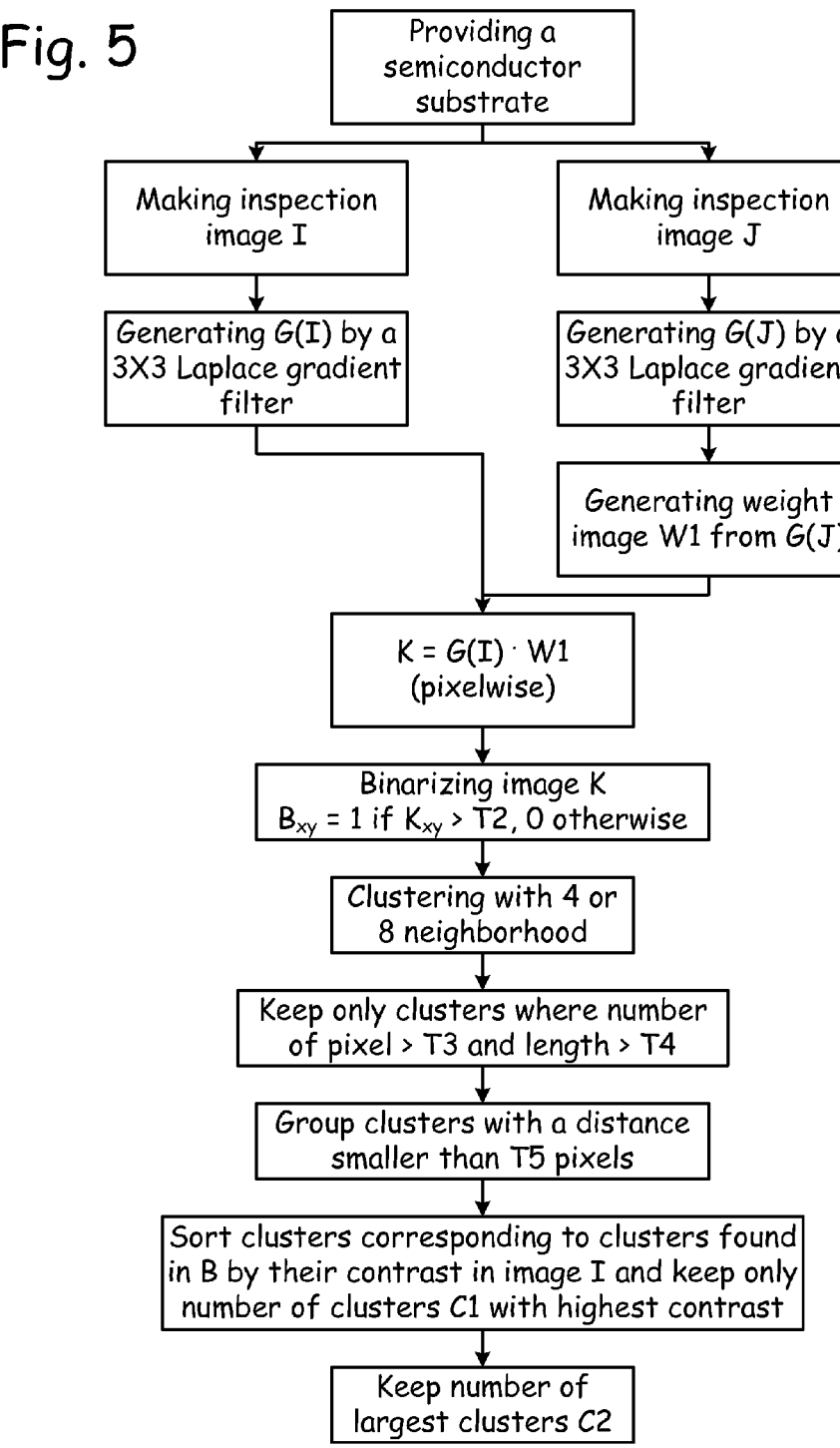
FIG. 5 illustrates a second example in accordance with the present invention.

As illustrated in FIG. 5, a second example in accordance with the present invention is described below.

A semiconductor substrate is provided on a means for holding a semiconductor substrate. The substrate is illuminated with a 950 nanometer backlight and an inspection image I is captured by a camera with a resolution between about 50 and about 100 micrometer/pixel. Then the substrate is illuminated with a diffuse 950 nanometer front light and an image J is captured by the same camera. Inspection image I, image J and all derived images have 8 bit grey values, i.e. from 0 to 255.

An image G(I) is then generated by a 3×3 Laplace convolution filter, for example $$\begin{array}{ccc} 1 & 1 & 1 \\ 1 & -8 & 1 \\ 1 & 1 & 1 \end{array}$$

which accentuates anomalies, such as cracks, voids, foreign material included in the substrate, and crystal boundaries from image I.

Further, an weight image W1 is generated by binarizing (threshold filtering) image G(J), which is a 3×3 Laplace convolution filtering image from J, wherein $$W1_{xy} = \begin{cases} 0 & \text{if } T6 < G_{xy}(J) \le T7 \\ 1 & \text{otherwise} \end{cases}$$

where preferably T6=150, T7=255 (both penetrating and non-penetrating cracks).

Hence G(I) and W1 are pixelwise multiplied in order to distinguish between crystal boundaries and other anomalies and the resulting image K is binarized wherein $$B_{xy} = \begin{cases} 1 \text{ if } K_{xy} > T2 \\ 0 \text{ otherwise} \end{cases}$$

where T2 is preferably 85.

The image I is examined using image B. Therefore, in image B clustering is done with 4 neighborhood (taking only 2 vertical and 2 horizontal neighborhood pixels in account) or 8 neighborhood (taking also diagonal neighborhood pixels in account). Of these cluster, only clusters where Number of pixels>T3 AND length>T4 are kept, with T3 is preferably 10 and T4 is preferably 20. Then, clusters with a distance smaller than T5 pixels are grouped, where T5 is preferably 3. Based on this group of clusters in image B, the corresponding clusters of pixels in image I are sorted by their contrast and only a number of clusters C1 (preferably 100) with the highest contrast are kept. Thereof, a number C2 (preferably 10) of the largest clusters are kept.

What is claimed is:

1. A method for detecting cracks in a polysilicon substrate comprising the steps of:
    a. making an inspection image I of the substrate with a back light emitting near infrared wavelengths, such that the cracks appear less transparent than the substrate,
    b. generating an image K by multiplying a high-pass convolution filtered image G(I) and a first weight image W1 that is generated by at least one of fuzzy weighting and binarizing of image I,
    c. generating an image B by binarizing image K, and
    d. determining locations of the cracks in the substrate by clustering image I using image B and selecting a number of highest contrast clusters, and
    e. designating the selected clusters as cracks.

2. The method according to claim 1, further comprising step a' of making an image J of the substrate, wherein the first weight image W1 is generated by at least one of fuzzy weighting and binarizing of a high-pass convolution filtered image G(J) from image J.

3. The method according to claim 2, wherein step a' further comprises illuminating the substrate with a diffuse front light emitting identical wavelengths as the back light.

4. The method according to claim 1 wherein the high-pass convolution filtered image G(I) is realized by 3×3 Laplacian convolution filtering.

5. The method according to claim 1, further comprising the step of multiplying the convolution filtered image G(I) with a second weight image W2 generated by at least one of fuzzy weighting and binarizing of image I.

6. The method according to claim 1, wherein the cracks comprise at least one of penetrating and non-penetrating micro-cracks.

7. An apparatus using the method according to claim 1.

* * * * *